(12) United States Patent
Karrman

(10) Patent No.: US 8,534,290 B2
(45) Date of Patent: Sep. 17, 2013

(54) HEARING PROTECTION

(75) Inventor: Elin Karrman, Umea (SE)

(73) Assignee: 3M Svenska Aktiebolag, Sollentuna (SE)

( * ) Notice: Subject to any disclaimer, the term of this patent is extended or adjusted under 35 U.S.C. 154(b) by 1692 days.

(21) Appl. No.: 11/915,098

(22) PCT Filed: May 24, 2006

(86) PCT No.: PCT/SE2006/000606
§ 371 (c)(1),
(2), (4) Date: Nov. 20, 2007

(87) PCT Pub. No.: WO2006/126945
PCT Pub. Date: Nov. 30, 2006

(65) Prior Publication Data
US 2010/0014686 A1      Jan. 21, 2010

(30) Foreign Application Priority Data
May 27, 2005   (SE) ........................... 0501205

(51) Int. Cl.
*A61F 11/06*   (2006.01)

(52) U.S. Cl.
USPC ........................................................ 128/867

(58) Field of Classification Search
USPC .................... 128/867, 857, 864, 866; 2/209; 381/71.6, 72, 73.1
See application file for complete search history.

(56) References Cited

U.S. PATENT DOCUMENTS

| | | | |
|---|---|---|---|
| 1,768,068 A | 6/1930 | Jauss | |
| 2,609,544 A * | 9/1952 | Berg | 2/209 |
| 2,672,864 A | 3/1954 | Makara | |
| 3,918,166 A * | 11/1975 | Mason | 33/514.2 |
| 4,037,273 A * | 7/1977 | Labaire | 2/209 |
| 5,038,412 A | 8/1991 | Cionni | |
| 5,243,709 A * | 9/1993 | Sheehan et al. | 2/209 |
| 5,685,021 A * | 11/1997 | Tsujino | 2/425 |
| 6,058,516 A * | 5/2000 | Purnell | 2/425 |
| D446,609 S | 8/2001 | Hill | |
| 6,338,723 B1 * | 1/2002 | Carpenter et al. | 602/75 |

OTHER PUBLICATIONS

International Search Report; PCT/SE2006/000606; Sep. 8, 2006.
Supplementary European Search Report from European Application No. 06747802 dated Apr. 27, 2010.

* cited by examiner

*Primary Examiner* — Patricia Bianco
*Assistant Examiner* — Raymond E Harris

(57) ABSTRACT

A hearing protection unit includes two sound damping cups for placing around a user's ears. A retainer device positions the cups and applies a compressive force on the cups. The retainer device includes a front band which extends between the front edge of each respective cup across the user's forehead, and a rear band which extends between the rear edge of each respective cup around the nape region of the user.

7 Claims, 4 Drawing Sheets

HEARING PROTECTION

TECHNICAL FIELD OF THE INVENTION

The present invention relates to hearing protection comprising two sound-damping cups for positioning around the user's ears, and a retainer device for positioning the cups and for applying a compressive force on the cups.

BRIEF DISCUSSION OF RELATED ART

Noise is becoming increasingly common in the community at large, and the awareness of the harmful effects of noise is increasing. The motivation for using hearing protection has increased correspondingly. The need for hearing protection exists not only at the workplace—although this is still the commonest situation where hearing protection is used. In principle, the hearing protection used hitherto has been adapted to different sectors of work, such as factory work, forestry work and military purposes. It has then become possible to use this form of protection for different purposes in the leisure and recreation sector. Examples of such purposes are work using gardening implements, in motor competitions, snow scooter driving, shooting and even at concerts.

The prior art hearing protection was originally developed for adults, which entails that their adaptation for use by children has been extremely limited.

In a modern society, it has proved that children often accompany adults in their activities, in particular if both of the parents take part in the care of the child. Human living habits are also still maintained after adults have had children. Thus, there is also a considerable need for hearing protection for children. However, ear plugs are less suitable for use by small children, partly because their acoustic meatus is extremely narrow and partly because of the risk of infection.

Granted, there are individual variations of hearing protection in the form of externally positioned ear cups that are intended for small children, but these are basically adaptations of hearing protection for adults where only the head strap positioned over the head of the wearer has been made shorter in order to adapt to the child's smaller head. However, such hearing protection is less appropriate for very small children, typically of the age groups from 0 to 4 years. On the one hand, the pressure from the retaining stirrup or strap on the ear cups is constant and generally too great for these small children and, on the other hand, the weight of the complete unit is often so great that the weak neck muscles of a child are not capable of supporting the child's head together with the hearing protection.

A further problem is that such small children are often carried in a perambulator or some form of car seat when hearing protection is used. The prior art hearing protection units are, in such instance, far too bulky to function satisfactorily. It is most often perceived as uncomfortable that the hearing protection jolts against the interior of the pram or the upholstery of the car seat when the child attempts to turn its head. As a result of the child's weaker neck muscles, the child's head, and as a result also the hearing protection ear cups, often jolt against surrounding objects. In addition, a contact between the hearing protection and surrounding objects generally gives rise to contact noise from the ear cup and this noise is not damped very efficiently by the hearing protection, and is often therefore perceived as extremely disturbing.

Another problem is that the prior art hearing protection units are difficult to wear under a cap, at the same time as small children often need some kind of hat or cap on the head. If the hearing protection is worn outside the cap, this often results in a less efficient sound damping, since the sealing ring of the hearing protection does not abut correctly against the skin around the ears.

Finally, there remains the problem of the lack of size adjustment of prior art hearing protection units.

BRIEF SUMMARY OF THE INVENTION

The invention provides a hearing protection unit which is comfortable and particularly suitable for small children.

The invention more particularly provides hearing protection which includes a retainer device having a front band that extends between the front edge of each respective cup over the forehead of the user, and a rear band that extends between the rear edge of each respective cup around the nape region of the user.

BRIEF DESCRIPTION OF THE ACCOMPANYING DRAWINGS

The present invention will now be described in greater detail hereinbelow, with particular reference to the accompanying Drawings. In the accompanying Drawings.

DETAILED DESCRIPTION OF THE INVENTION

Figure 1:
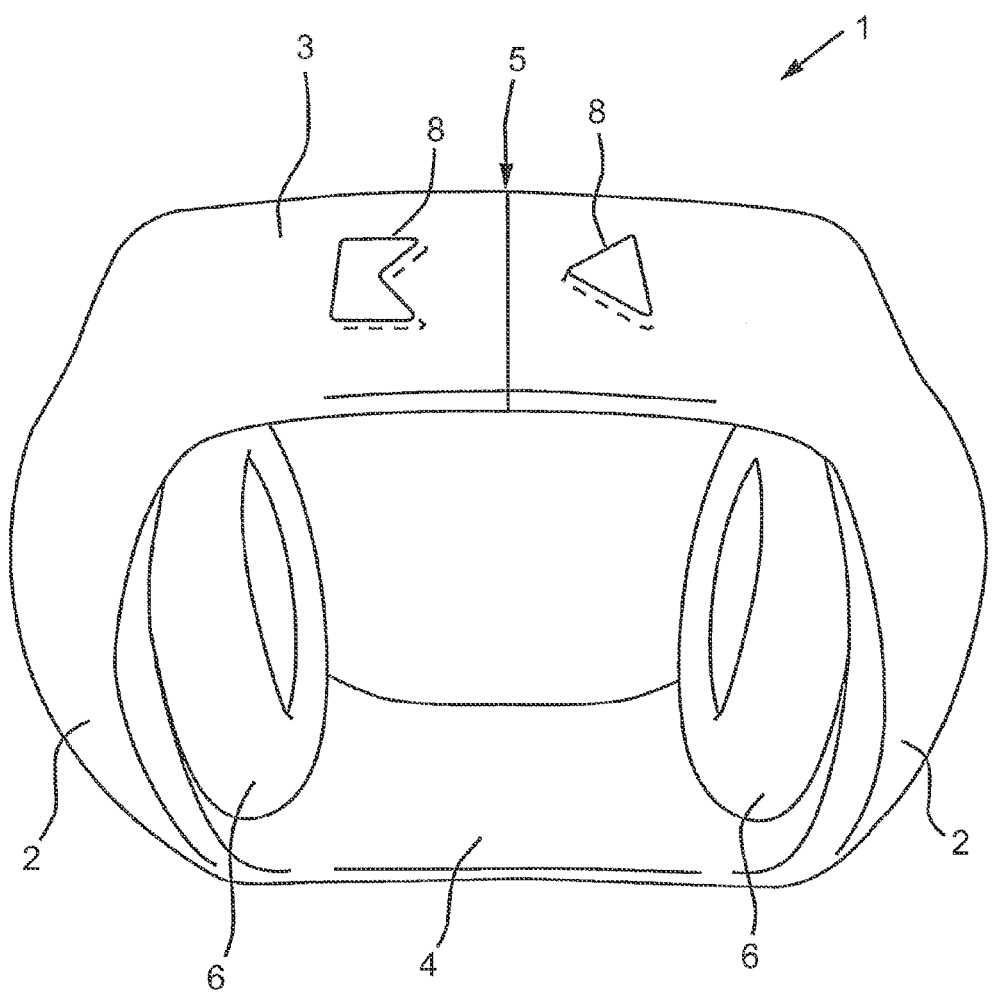
FIG. 1 is a straight front elevation of the hearing protection unit according to the present invention.

FIG. 1 shows a hearing protection unit 1 according to the invention, whose major components are as follows. For the most important function of the hearing protection unit 1, namely sound damping, two cups 2 are disposed each on one side of the hearing protection unit 1, for abutment around the area surrounding the user's ears. Between the front edges of the cups 2, in that position which the hearing protection unit 1 is intended to assume when in use, there extends a front band 3. The front band 3 is intended to run across the forehead of the user and is provided with an opening buckle or clamp 5.

In a corresponding manner, a rear band 4 extends between the rear edges of the cups 2 and is in turn adjustable, on the one hand for adapting the size of the hearing protection unit 1 and, on the other hand, for adapting the pressure of the hearing protection 1 against the user's head. The adjustment device for this purpose is, however, not visible in FIG. 1. Together, the front band 3 and the rear band 4 constitute the basis of the retainer device that retains the hearing protection on the user's head.

Figure 2:
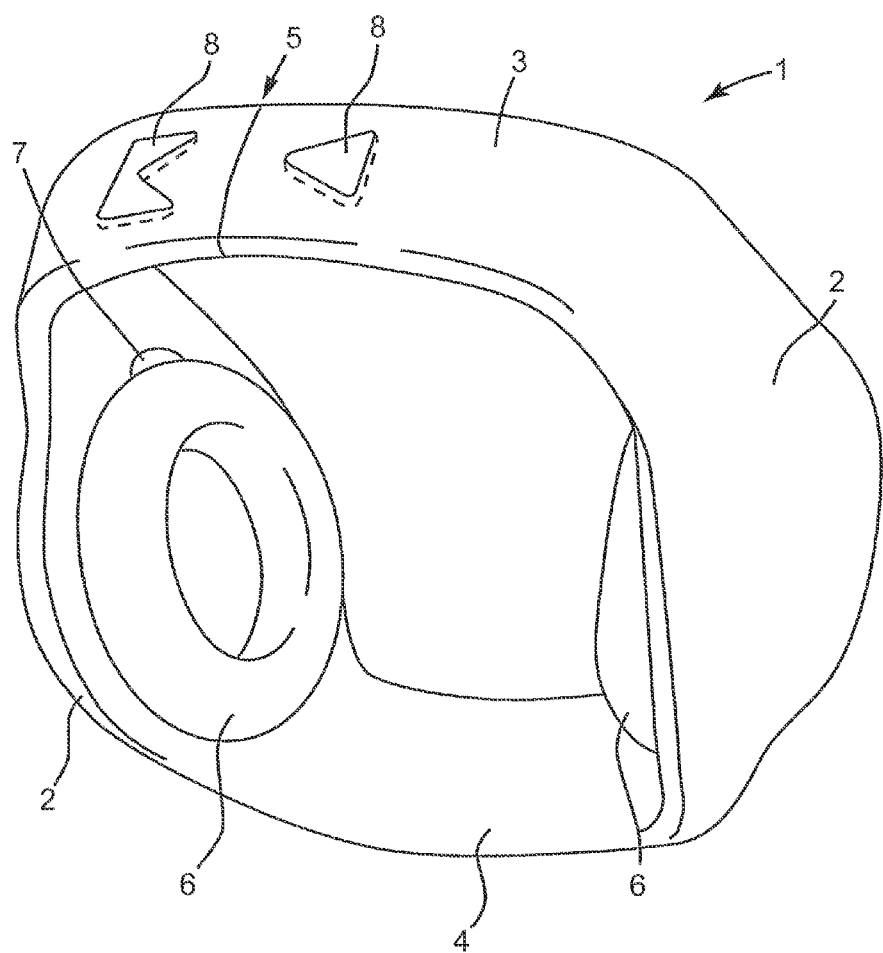
FIG. 2 is a perspective view obliquely from the front of the hearing protection unit according to the present invention.

FIG. 2 is a perspective view of the hearing protection unit 1. It will be clearly apparent here that the cups 2 are, in the preferred embodiment, clad with a material 11, preferably fabric, on their outsides. The fabric minimizes the risk that the cups 2 will catch in surrounding objects when the user moves its head, and moreover reduces scratching noise which occurs on contact between surrounding objects and the cup 2. The material 11 also contributes in imparting a pleasant appearance to the hearing protection unit 1.

In addition, each ear cup 2 displays a sealing ring 6 on the inside of the hearing protection unit 1. The ring 6 serves to seal against the area surrounding the user's ear, in order to maximize the sound damping effect of the hearing protection unit 1

The ring 6, which may be of a type that is common in prior art hearing protection, is provided with a flap or tab 7 in order to facilitate removal thereof from the hearing protection unit 1. Such a removal is used on cleaning, possibly washing, of the hearing protection unit 1.

The front band 3 extends from the front edge of each respective cup 2, preferably from the upper region of the front edge, and further across the user's forehead, or at least the front area of the user's head. Somewhere on the front band 3, in the preferred embodiment in the centre, the opening buckle or clamp 5 is disposed. The opening buckle or clamp 5 may be of any optional catch or snap action type that occurs on the market. In the illustrated embodiment the opening buckle or clamp 5 is clad with fabric, like the cups, and the rest of the front band 3, in order to create a unitary and aesthetically attractive appearance, but also to reduce the risk that the opening buckle or clamp 5 catches in surrounding objects. At the site of the opening buckle or clamp 5, the front band 3 may be provided with some type of marking 8, for example a printed or embossed marking. This marking 8 serves to clarify the opening function of the opening buckle or clamp 5.

Figure 3:
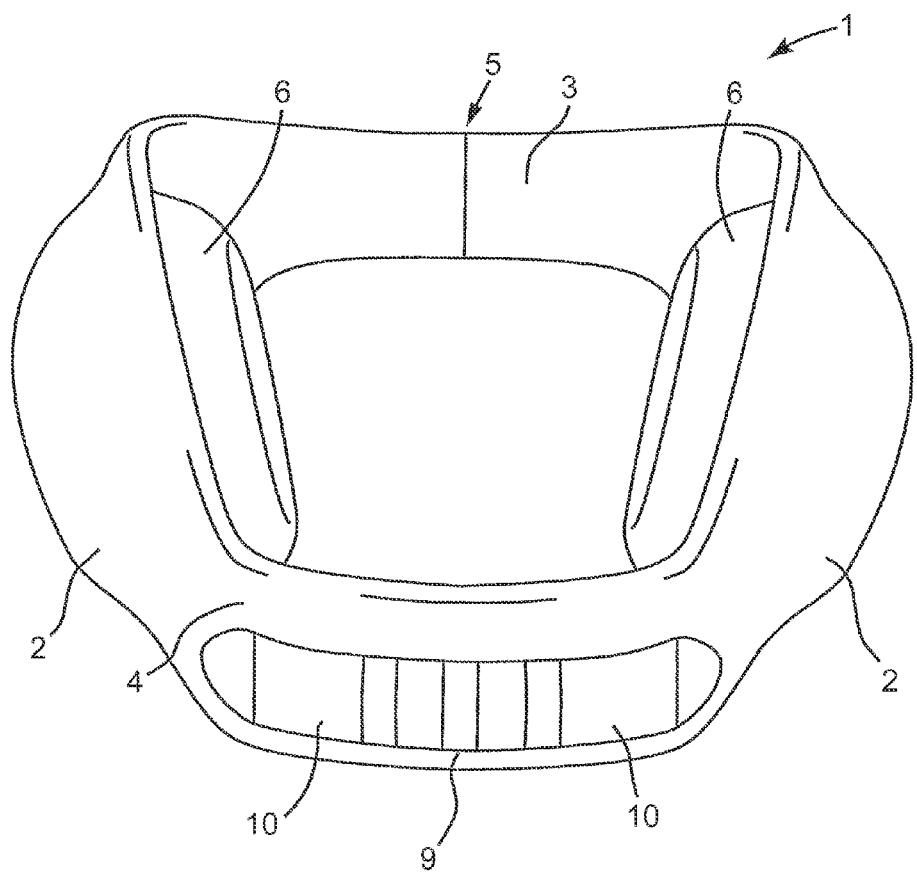
FIG. 3 is a rear elevation of the hearing protection unit according to the present invention.

FIG. 3 is a rear elevation of the hearing protection unit 1 according to the present invention. Here, the rear band 4 is seen from the outside. The rear band 4 extends from the rear edge of each respective cup 2 and around the back of the user's head or the user's nape region. The stretching should preferably be such that it is comfortable to wear, gives a satisfactory tightening between the sealing ring 6 and the user's head and does not unnecessarily move or slip upwards when the user moves. Preferably, the rear band 4 starts from lower, rear regions of the cups 2.

An adjustment device 9 is also provided on the rear band 4, for realizing the desired adjustable feature of the hearing protection unit 1. The adjustment device 9 is disposed in conjunction with an elastic band 10 which extends inside the outer textile material 11, over each respective cup 2 and up through the front band 3 until it reaches the centrally positioned opening buckle or clamp 5. The adjustment device 9 is adjustable for realizing a variable fit of the hearing protection unit 1 so that it may be used on different head sizes. In children, the head size is extremely dependent on the age of the child, at least in small children whose head grows relatively quickly, in particular the back of the head, and the possibility of adjustment of the hearing protection unit 1 is particularly important for these age groups. Correspondingly, it is of interest for these age groups that the pressure against the head is not excessive, not least for reasons of comfort, but also because the cranium or fontanel bones have not yet grown together and that a deformation of the head could occur in the event of lengthy pressure against the head.

Figure 4:
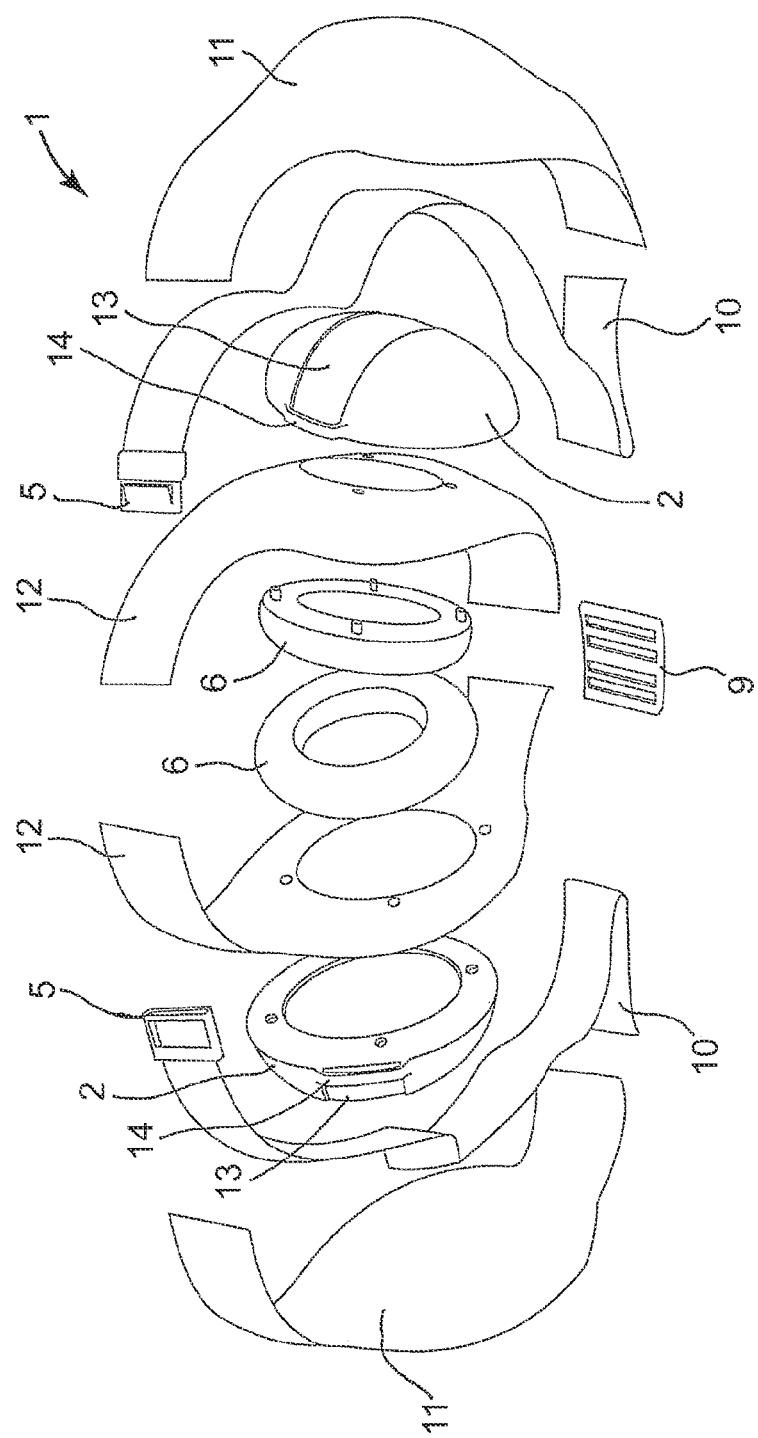
FIG. 4 is an exploded view of the hearing protection unit.

FIG. 4 is an exploded view of the hearing protection unit 1. The hearing protection unit 1 is substantially symmetric about a central plane, possibly with the exception of the components included in the opening buckle or clamp 5. In the exploded view, the removable sealing ring 6 is clearly visible, which abuts against the side of the user's head. In addition, the outer fabric 11 is shown, as well as an inner lining 12 which together constitute the visible parts of the retainer device for the hearing protection unit 1. The outer textile 11 is disposed to surround the cup 2 and is advantageously slightly elastic. The inner lining 12 is, in the area of the cup 2, provided with an opening to the inside of the cup 2, in which opening additional damping material may be disposed, as is common in hearing protection ear cups. Also the inner lining 12 may display a certain elasticity. The materials in both the outer fabric 11 and the inner lining 12 are advantageously selected so that they are suitable for use within a broad temperature range. Possibly, some part of the outer fabric may be reflecting.

The ear cup 2 is provided with a groove 13 on its outside. The groove 13 extends substantially horizontally across the cup so that a pressure that is applied therein is distributed substantially uniformly to the sealing ring 6. The groove 13 is in the form of a broad depression in the outside of the cup material. Moreover, slots 14 are provided at the edges of the cup 2 which at the same time constitute the ends of the groove 13.

The band 10 extends through the slots 14 and in the groove 13. This band 10 is elastic, preferably to a higher degree than in the outer fabric 11 and the inner lining 12. The compressive force on the ear cups 2 in order to realize an acceptable seal is preferably achieved with the aid of the elastic band 10. The band 10 extends through both the front band 3 and the rear band 4, between the outer fabric 11 and the inner lining 12. Both ends of the elastic band 10 are secured, on the one hand in the opening buckle or clamp 5 and on the other hand in the adjustment device 9. Since the elastic band 10 is slidable in the groove 13 and through the slots 14, the pressure from the band 10 will be uniformly distributed around the head and on the ear cups 2, even after an adjustment of the length of the band 10 in the adjustment device 9.

When the band is tightened with the aid of the adjustment device 9, the fit form will be tighter and moreover the pressure will be higher for one and the same head size. In order to attain a suitable adjustment, the band 10 is advantageously calibrated, for example with a scale which corresponds to the circumference of the head of the user in centimeters, or a scale which indicates the user's age and which is based on the relationship between average head sizes for different ages. Advantageously, the calibration is such that, at a certain adjustment that corresponds to a certain head size, it also provides a suitable compressive force on the ear cups 2, i.e. which does not risk being too high, but which nevertheless provides an adequate seal.

It is also possible to carry out an adjustment in two stages, the first stage comprising measuring the actual size of the head, in other words the band 10 abuts only lightly against the head. In the second stage, the band 10 is tightened further a predetermined length so that the pressure against the head will be correct and a desired sound damping is attained. The first stage may possibly be omitted if the head size of the child is already known.

The present invention may naturally also be altered in size so that it is usable substantially for adults. Adults need to wear the hearing protection unit 1 according to the present invention as well, since the hearing protection unit 1 is typically easier than other forms of hearing protection to wear under a hat or cap, which may be an advantage in noisy outdoor activities such as, for example, snow scooter driving. Another conceivable field of use for the hearing protection unit 1 by adults is to be used by people who need to sleep with hearing protection. For example, shift workers who need to sleep in the daytime may find the hearing protection according to the present invention useful.

Even other modifications in appearance will not affect the function of the hearing protection unit 1 according to the invention either. For example, it is conceivable that the cups 2 are only partly clad with textile material. The positioning of the opening buckle or clamps 5 and adjustment device 9 may be reversed or otherwise varied. It is also possible even to completely dispense with the opening buckle or clamp 5 and only make the hearing protection adjustable. For removing and wearing the hearing protection it is then necessary that the elasticity of the material included in the retainer device is sufficiently high. Another variation is that the hearing protection is manufactured in a large number of sizes in order to obviate the need for the adjustment device 9.

The sealing rings 6 need not necessarily be removable from the hearing protection unit 1. Instead, they may be of one piece manufacture with the cups 2 or be glued or welded in place against them.

The present invention may be modified further without departing from the scope of the appended Claims.

What is claimed is:

1. Hearing protection comprising:
   two sound-damping cups for positioning around a user's ears;
   a retainer device for positioning the cups and for applying a compressive force on the cups comprising an inner layer of textile, an outer layer of textile and
   an elastic band comprising a front band that extends between a front edge of each respective cup over the forehead of the user, and a rear band that extends between a rear edge of each respective cup around a nape region of the user, wherein the elastic band is calibrated for adaptation by the user; and
   a sealing ring;
   wherein the sound-damping cups are positioned between the inner layer of textile and the outer layer of textile, and the sealing ring is not positioned between the inner layer of textile and the outer layer of textile.

2. The hearing protection as claimed in claim 1, wherein the elastic band runs in a groove on the outsides of the cups.

3. The hearing protection as claimed in claim 1, wherein an adjustment device is placed on the rear band.

4. The hearing protection as claimed in claim 3, wherein an openable clamp is provided separately from the adjustment device.

5. The hearing protection as claimed in claim 4, wherein the openable clamp is disposed in the front band.

6. The hearing protection as claimed in claim 1, wherein the retainer device is openable for removing and applying the hearing protection.

7. The hearing protection as claimed in claim 1, wherein the retainer device at least partly extends on the outside of the cups in order to protect them against direct contact with surroundings.

* * * * *